United States Patent [19]

Rölla et al.

[11] 4,218,434

[45] Aug. 19, 1980

[54] METHOD OF CLEANING TEETH AND COMPOSITIONS FOR USE IN SUCH METHOD

[75] Inventors: Gunnar Rölla, Oslo, Norway; Michael R. C. Winter, Macclesfield, England

[73] Assignee: Imperial Chemical Industries Limited, London, England

[21] Appl. No.: 916,937

[22] Filed: Jun. 19, 1978

[30] Foreign Application Priority Data

Jun. 23, 1977 [GB] United Kingdom ............... 26308/77

[51] Int. Cl.$^2$ ............................................. A61K 7/16
[52] U.S. Cl. ...................................................... 424/49
[58] Field of Search ..................................... 424/49–58

[56] References Cited

U.S. PATENT DOCUMENTS

| | | | |
|---|---|---|---|
| 3,004,897 | 10/1961 | Shore ..................................... | 424/49 |
| 3,151,027 | 9/1964 | Cooley et al. .......................... | 424/23 |
| 3,751,568 | 8/1973 | Mundorff et al. ..................... | 424/131 |
| 4,080,440 | 3/1978 | Digivilo et al. ........................ | 424/49 |
| 4,083,955 | 4/1978 | Grabanstetter et al. .............. | 424/49 |

FOREIGN PATENT DOCUMENTS

| | | | |
|---|---|---|---|
| 997488 | 1/1952 | France ..................................... | 424/49 |
| 2297631 | 1/1976 | France ..................................... | 424/57 |
| 1310967 | 3/1973 | United Kingdom . | |
| 1452125 | 10/1976 | United Kingdom . | |
| 1516525 | 7/1978 | United Kingdom ...................... | 424/49 |

OTHER PUBLICATIONS

Olsson et al., Arch. Oral. Biol. 22: 461–466 (1977).
Castillo-Mercado et al., Arch. Oral Biol. 18: 629–640 (1973).
Losee et al., N.Y. State Dent. J., 36: 15–19 (1970).
McCann, Arch. Oral. Biol. 14: 521–531 (1969).
Manly et al., J. Dent. Res. 28: 160–171 (1949).
Losee et al., Chem. Abstr. 84, No. 133258w (1976).
Basalaeva et al., Chem. Abstr. 83, #143739x (1976).
Skorland et al., Scand. J. Dent. Res. 86: 103–107 (1978) "Effect of Some Polyvalent Cations on Plaque Formation in Vivo".

*Primary Examiner*—Shep K. Rose
*Attorney, Agent, or Firm*—Cushman, Darby & Cushman

[57] ABSTRACT

The invention relates to a method of cleaning teeth by applying thereto one or more elements selected from yttrium, scandium and lanthanum and the lanthanides, and to compositions, such as mouthwashes, toothpastes and dental gels, for use in such a method.

2 Claims, No Drawings

METHOD OF CLEANING TEETH AND COMPOSITIONS FOR USE IN SUCH METHOD

This invention relates to dental hygiene, and more particularly it relates to a method of cleaning teeth.

It is known that a wide variety of elemental cations, including those derived from gallium, yttrium, lead, indium, beryllium, cerium, dysprosium, iron, arsenic, thorium, iridium, rubidium, vanadium, zirconium, titanium, tin, thallium, aluminum, copper, ruthenium, gold, samarium, rhodium, mercury, lithium, cobalt, lanthanum, uranium, zinc, barium, caesium, strontium, calcium, cadmium and chromium, reduce the acid solubility of tooth enamel in an in vitro test system (R. S. Manly and B. G. Bibby, *J.Dent.Res.*, 1949, 28, 160–171). It is also known that tooth enamel may be remineralised by sequential application to the teeth of a cationic and an anionic component which react below the tooth surface to form an insoluble salt. Examples of the cationic component are ions derived from barium, lanthanum, manganese, lead, tin, zinc, indium, zirconium, iron, titanium, vanadium and cadmium (UK Patent specification No. 1,452,125).

It has been found that administration of yttrium nitrate to rats, either by intraperitoneal injection or via the drinking water, reduces the incidence of caries and this effect has been attributed to the incorporation of yttrium into the dental enamel, thus reducing its acid solubility. (R. Castillo Mercado and T. G. Ludwig, *Archs.oral Biol.*, 1973, 18, 637–640). It has also been found that mouthrinsing with a stannous fluoride solution reduces plaque formation on tooth enamel (N. Tinanoff, J. M. Brady, and A. Gross, *Caries Res.*, 1976, 10, 415–426; N. Tinanoff, *J.Dent.Res.*, 1977, 56, Spec. Issue A, A138).

It has now been discovered, and herein lies our invention, that deposits such as dental plaque may be removed from the surface of teeth, or may be prevented from adhering thereto, by application of a cation of a selected group of elements.

According to the invention there is provided a method of cleaning teeth by applying thereto a cation of one or more elements selected from yttrium, scandium and lanthanum and the lanthanides. The lanthanides include cerium, praseodymium, neodymium, promethium, samarium, europium, gadolinium, terbium, dysprosium, holmium, erbium, thulium, ytterbium and lutetium. These elements are very closely related chemically since they all fall within Group IIIb of the Periodic Table. Lanthanum and the lanthanides form the first group of Inner Transition Elements within Group IIIb.

The method of the invention is particularly useful for cleaning teeth in human beings. The efficent cleaning of teeth is, of course, of immense cosmetic value. One of the substances routinely found on the surface of teeth is bacterial plaque and the method of this invention is particularly useful in removing plaque from teeth or in preventing its adhering thereto. The method of the invention is also useful in removing various types of stain from teeth, for example the stain produced by smoking tobacco. In addition, bacterial plaque is generally regarded as a dominant etiological factor in caries and periodontal disease and removal of plaque from teeth or prevention of its accumulation is known to have a beneficial effect in those conditions.

Only a very small proportion of the population of an industrialised country is free from caries or periodontal disease, and it is to be expected therefore that, for the majority of that population, application of the method of the invention will result in the additional benefit of a reduction in the incidence of caries and/or periodontal disease.

The preferred cations for use in the method of the invention are those derived from lanthanum and the lanthanides, and a particularly preferred cation is the lanthanum cation.

When used in the method of the invention, the cation may be in the form of a salt, and preferably in the form of a water-soluble salt. Examples of such water soluble salts are the chloride, bromide, iodide, nitrate, acetate or sulphate. The cation may also be used in the form of a salt with an antibacterial anion.

The preferred compound for use in the method of the invention is lanthanum chloride, $LaCl_3$.

The amount of cation used in the method of the invention may vary from 0.01 m.moles to 1 m.moles of cation and preferably from 0.1 m.moles to 0.5 m.moles of cation, and it may be applied from once a week to 1 to 10 times per day. A preferred regime is three times per day, after meals, or failing this, twice per day, night and morning.

The method of the invention achieves a satisfactory result simply by application of the cation to the teeth, for example in the form of a simple aqueous solution. However, an improved degree of cleansing can be achieved if the method of the invention is combined with one or more of the normal mechanical methods of cleaning teeth, for example if combined with the use of a toothbrush, toothpick, dental floss, dental probe or rotary dental brush. A particularly preferred adjunct to the method of the invention is the use of a toothbrush.

The cation for use in the method of the invention may be presented in the form of a composition such as a simple aqueous solution or suspension or in the form of a more sophisticated composition such as a mouthwash, toothpaste, prophylaxis paste, toothpowder, pastille, chewing gum or oral spray, or it may be incorporated into a beverage, nutritional substance or confection. It may also be incorporated into the public water supply.

The compositions described above are those which are well known to those skilled in this art. They may incorporate any of the ingredients normally used in such compositions, with the addition of the cation in the form of a salt. In the case of a mouthwash or oral spray the cation is incorporated at the desired user concentration. In the case of a toothpaste, prophylactic paste, toothpowder, lozenge or chewing gum, it may be necessary, depending on the nature of the ingredients in the composition, to increase the concentration of the cation to above the level of the desired user concentration, for example by up to five times the desired user concentration, in order to allow for incomplete availability of the cation in use as a result of specific binding of the cation to one or more of the ingredients. In these formulations it is preferable to use ingredients which avoid precipitation of the cation in the form of an insoluble salt.

A typical mouthwash has an aqueous base and generally incorporates a thickener and a flavour.

A gel has an aqueous base and generally incorporates a gelling agent, a surfactant, a flavour and a preservative.

A toothpaste has an aqueous base and generally contains an abrasive, a binder, a thickener, a surfactant, a humectant, a flavouring agent and a sweetening agent.

Specific compositions are described, by way of example only, in Examples 6 to 9.

According to a further feature of the invention there is provided a composition for use in the method of cleaning teeth described above which is in a form for use in a non-sequential manner. By the words "in a form for use in a non-sequential manner" we mean, for example, that the composition is presented as a single pack which is intended to be used on its own, and is not intended to be used immediately before or immediately after a second different composition in a sequential manner. It is not, for example, part of a two-component pack, and it is not a single composition which is designed to release separately two components in a sequential manner. On the contrary the composition of the invention is, for example, a simple aqueous solution or suspension, or a more sophisticated composition such as a mouthwash, toothpaste, prophylaxis paste, toothpowder, lozenge, chewing gum or oral spray which is presented in a single pack for use on its own. The pack may optionally carry instructions on how the composition should be used for cleaning teeth according to the method of the invention, and such instructions may indicate that the composition should be used in a non-sequential manner. The instructions will be appropriate to the nature of the composition. Thus, for example, if the composition is a toothpaste the instructions may indicate that the user should use the paste as the sole agent for brushing his or her teeth.

The invention is illustrated, but not limited, by the following Examples:

EXAMPLE 1

Sixty dental students, average age 19 years, volunteered for the experiment. After having had a thorough prophylaxis, all the students were instructed to suspend oral hygiene for 3 days. To provoke plaque formation the students rinsed with 10 ml. of 15% w/v aqueous sucrose solution for 1 minute every second hour between 8 a.m. and 10 p.m. At the end of this period the amount of plaque which had accumulated on the teeth was estimated by use of a Plaque Index, as follows:

0—No firmly attached plaque
1—No firmly attached plaque visible, but some collected with a dental probe
2—Slight amount of firmly attached plaque visible
3—Extensive amount of firmly attached plaque visible.

The 16 individuals showing the highest Plaque Index values were selected for further study over a period of 4 days. At the start of this period, the participants were brought to Plaque Index=0. During the test, no oral hygiene was allowed, and in addition to the sucrose rinses, 2 daily rinses with 10 ml. of 20 m.molar aqueous lanthanum chloride solution were instituted in a group of 8 individuals, the remaining 8 acting as controls. At the end of the 4 day period, plaque estimations were made by one person, the results being statistically averaged. The whole experiment was carried out under double blind conditions.

The control group had a mean Plaque Index of 1.0 whereas the treated group had a mean Plaque Index of zero. The very small amount of deposit which was present in the treated group was very loosely attached to the tooth surface and could be blown off with an air jet.

In a parallel experiment, individuals who rinsed with a 20 m.molar solution of aqueous stannous fluoride had a mean Plaque Index of 0.3.

EXAMPLE 2

A test panel of ten volunteers had a thorough prophylaxis to remove plaque from their teeth so that the Plaque Index measured according to Loe, *J.Periodontol.*, 1967, 38, 610–616, was zero at the start of the experiment. The panel was provided with new toothbrushes and instructed to brush their teeth each morning and evening for 30 seconds over a period of four days, according to each individual's own habits, with a 10 ml. test solution, and then to rinse the teeth with the remainder of the test solution. The test solutions were 20 mM aqueous NaCl, 10mM aqueous $LaCl_3$, 20 mM aqueous $LaCl_3$ and 20 mM aqueous $YCl_3$. The whole experiment was carried out under double blind conditions, each person using one of the test solutions in turn. Each person's Plaque Index was brought to zero before using a new test solution. The results obtained were as follows:

| Volunteer Number | Plaque Index | | | |
| --- | --- | --- | --- | --- |
| | 20 mM NaCl | 10 mM $LaCl_3$ | 20 mM $LaCl_3$ | 20 mM $YCl_3$ |
| 1 | 0.88 | 0.43 | 0.30 | 0.41 |
| 2 | 1.12 | 0.63 | 0.44 | 0.54 |
| 3 | 0.68 | 0.48 | 0.31 | 0.30 |
| 4 | 1.09 | 0.63 | 0.45 | 0.59 |
| 5 | 1.02 | 0.83 | 0.52 | 0.50 |
| 6 | 0.62 | 0.60 | 0.48 | 0.60 |
| 7 | 0.88 | 0.62 | 0.32 | 0.48 |
| 8 | 0.55 | 0.42 | 0.34 | 0.42 |
| 9 | 0.90 | 0.66 | 0.46 | 0.60 |
| 10 | 0.84 | 0.88 | 0.62 | 0.60 |

EXAMPLE 3

In a parallel experiment solutions of 20 mM aqueous $GdCl_3$ and aqueous $YbCl_3$ were tested in groups of four people according to the protocol described in Example 2. The results obtained were comparable with those obtained for $YCl_3$ in Example 2.

A similar result was obtained using 20 mM $La_2(SO_4)_3$ though a complete solution at this concentration was not achieved.

EXAMPLE 4

A test panel of 10 volunteers all of whom had intact buccal surfaces on their upper and lower teeth, first molar to first molar inclusive, were separated into two groups (A and B) having five persons in each.

On Day 0 each person's mouth and teeth was stained with a plaque disclosing agent, erythrosine and then each person had a thorough prophylaxis in order to reduce to zero the Gingival margin Plaque Index measured according to Harrap, *J.Clin.Periodontol.*, 1974, 1, 166–174.

On Days 1 and 2 each person was instructed to brush their teeth as normal with their own toothbrush and toothpaste. They were then re-examined to ensure the presence of healthy gingiva, and their Gingival margin Plaque Index was again reduced to zero.

On Day 3, at 7 a.m., each group brushed their teeth with 20 ml. of either a 20 mM aqueous lanthanum acetate solution or water respectively with a new soft toothbrush dipped in the respective test solution. Rinsing for 1 minute was then carried out with the remainder of the test solution. No after-rinses with water were permitted.

On Day 4, at 1 pm., each person's teeth was stained with disclosing agent and the Gingival margin Plaque Index scored, the scoring being performed blindly.

Days 1 to 4 of the test period were repeated, groups A and B interchanging test solutions.

The results obtained were as follows, the figures in the second and third column being a summation of the percentage score for each of the 24 teeth.

| Volunteer Number | Gingival margin Plaque Index | | |
|---|---|---|---|
| | 20 mM lanthanum acetate | Water | Difference |
| 1 | 140 | 140 | 0 |
| 2 | 390 | 470 | − 80 |
| 3 | 110 | 770 | −660 |
| 4 | 530 | 1610 | −1080 |
| 5 | 1930 | 2130 | −200 |
| 6 | 1170 | 1760 | −590 |
| 7 | 240 | 370 | −130 |
| 8 | 1300 | 1300 | 0 |
| 9 | 520 | 490 | + 30 |
| 10 | 750 | 280 | +470 |

EXAMPLE 5

A subject rinsed his mouth and teeth with 10 ml. of 20 mM aqueous $LaCl_3$ solution for 1 minute. The solution tasted salty but was not unpleasant—there was no metallic taste. After rinsing the subject spat out pieces of organic debris. His mouth and teeth felt much cleaner and in particular his teeth felt dry and clean.

On a separate occasion the same subject rinsed with 10 ml. of 20 mM aqueous stannous fluoride. The solution tasted acid and metallic. The cleansing effect experienced with stannous fluoride was not as great as that with $LaCl_3$.

A different subject found that rinsing with 20 mM aqueous $LaCl_3$ solution significantly reduced the amount of tooth stain caused by smoking tobacco.

EXAMPLE 6

| Mouthwash | % w/v unless otherwise stated |
|---|---|
| $LaCl_3 . 7H_2O$ | 0.74 |
| Sorbitol Solution | 30.0 |
| Ethyl Alcohol 95% v/v | 7.0% v/v |
| Peppermint Flavour | 0.1 |
| Ponceau 4R | 0.001 |
| Purified Water to | 100 |

EXAMPLE 7

| Dental Gel | % w/v |
|---|---|
| $LaCl_3 . 7H_2O$ | 1.0 |
| Hydroxyethylmethyl Cellulose | 3.0 |
| Isopropanol | 4.0 |
| Spearmint Oil | 0.05 |
| Polysorbate 80 | 0.5 |
| Purified Water to | 100 |

EXAMPLE 8

| Toothpaste | % w/v |
|---|---|
| $LaCl_3 . 7H_2O$ | 1.5 |
| Alumina | 33.0 |
| Sorbitol Solution | 30.0 |
| Colloidal Silicon Dioxide | 1.5 |
| Hydroxyethylcellulose | 0.5 |
| Isopropanol | 4.0 |
| Polyoxyethylene 50 Stearate | 2.0 |
| Spearmint Oil | 0.1 |
| Sodium Saccharin | 0.05 |
| Water to | 100 |

EXAMPLE 9

| Pastille Base | % w/w |
|---|---|
| $LaCl_3 . 7H_2O$ | 0.1 |
| Gelatin | 35.0 |
| Glycerol | 25.0 |
| Citric Acid | 2.0 |
| Sodium Benzoate | 0.2 |
| Lemon Oil | 0.1 |
| Menthol | 0.05 |
| Water to | 100 |

What we claim is:

1. In a method of cleaning dental plaque or stains, including tobacco stains, from human teeth by applying thereto in a plaque index regime of applications, from once a week, to 10 times per day, an aqueous composition which is in a form for use in a non-sequential manner and consists essentially of an effective amount of an unbound cation, in the form of a dissolved water soluble salt, said composition and said regime being substantially free from any ingredients which precipitate the cation as a water-insoluble salt, continuing the application until plaque or stains including tobacco stains, are removed and then orally discharging the composition, the improvement wherein said plaque or stains including smoking tobacco stains on said human teeth are removed, and no firmly attached plaque remains, by cleaning, brushing or rinsing said human teeth with a user concentration from about 0.01 m. moles to about 1 m. moles of said cation in the form of lanthanum chloride acetate or sulfate, yttrium chloride, ytterbium chloride, or gadolinium chloride, while said user avoids insoluble salt precipitation of said cation during said regime.

2. A method as claimed in claim 1 wherein the cation is the lanthanum cation.

* * * * *